US00PP32178P2

(12) United States Plant Patent
Koning

(10) Patent No.: US PP32,178 P2
(45) Date of Patent: Sep. 8, 2020

(54) ***LAVANDULA* PLANT NAMED 'SAKO1638'**

(50) Latin Name: *Lavandula angustifolia*
Varietal Denomination: sako1638

(71) Applicant: Lammert Koning, Nuis (NL)

(72) Inventor: Lammert Koning, Nuis (NL)

(73) Assignee: L. KONING BEHEER B.V., Nuis (NL)

( * ) Notice: Subject to any disclaimer, the term of this patent is extended or adjusted under 35 U.S.C. 154(b) by 0 days.

(21) Appl. No.: 16/602,699

(22) Filed: Nov. 21, 2019

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445
See application file for complete search history.

*Primary Examiner* — Susan McCormick Ewoldt
(74) *Attorney, Agent, or Firm* — C. A. Whealy

(57) ABSTRACT

A new and distinct cultivar of *Lavandula* plant named 'sako1638', characterized by its compact and upright plant habit; strong and sturdy plants; freely branching growth habit; freely flowering habit; dark violet-colored flowers positioned on strong and erect peduncles; and good garden performance.

2 Drawing Sheets

Figure 1:
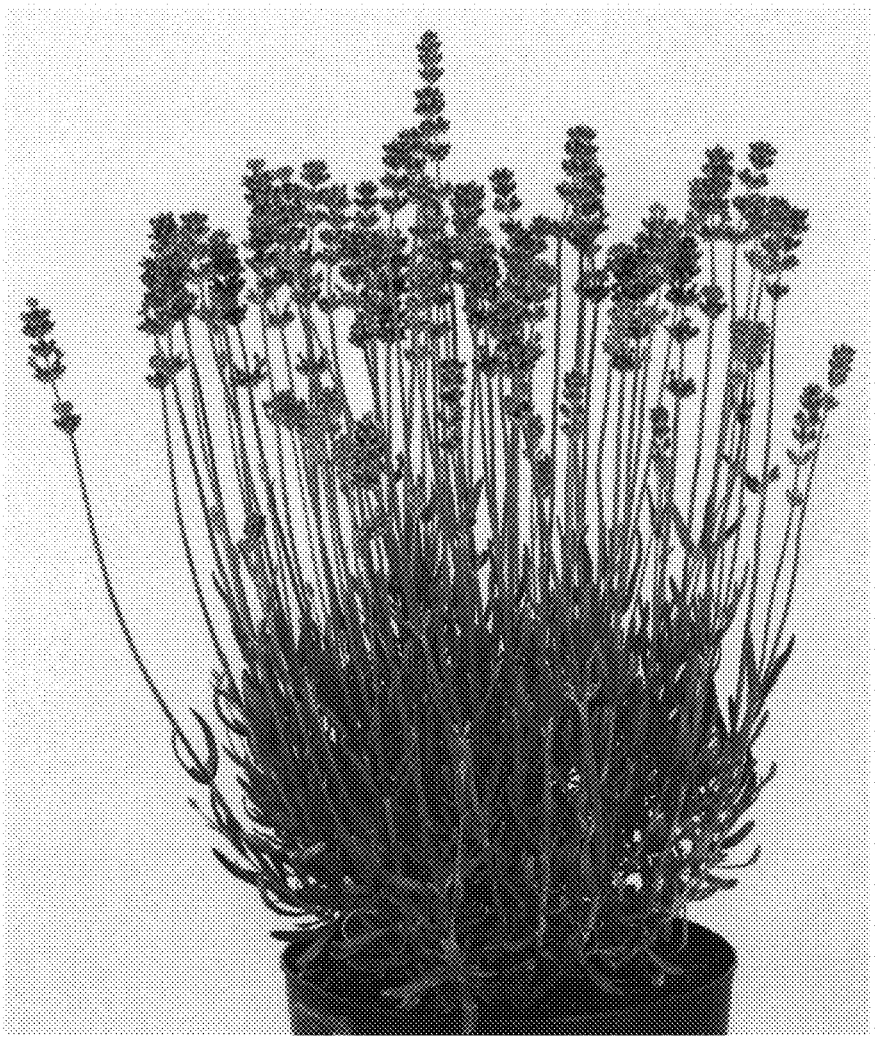

Botanical designation: *Lavandula angustifolia.*
Cultivar denomination: 'sako1638'.

BACKGROUND OF THE INVENTION

The present invention relates to a new and distinct *Lavandula* plant, botanically known as *Lavandula angustifolia*, commonly referred to as English Lavender and hereinafter referred to by the name 'sako1638'.

The new *Lavandula* plant is a product of a planned breeding program conducted by the Inventor in Boskoop, The Netherlands. The objective of the breeding program was to develop new unique *Lavandula* plants with good performance and attractive plant form and flower coloration.

The new *Lavandula* plant originated from an open-pollination in June, 2015 of *Lavandula angustifolia* 'Felice', not patented, as the female, or seed, parent with an unknown proprietary selection of *Lavandula angustifolia* as the male, or pollen, parent. The new *Lavandula* plant was discovered and selected by the Inventor as a single flowering plant within the progeny of the stated open-pollination in a controlled environment in Boskoop, The Netherlands in July, 2016.

Asexual reproduction of the new *Lavandula* plant by terminal stem cuttings in a controlled greenhouse environment in Boskoop, The Netherlands since August, 2016 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'sako1638' as a new and distinct *Lavandula* plant:

1. Compact and upright plant habit.
2. Strong and sturdy plants.
3. Freely branching growth habit.
4. Freely flowering habit.
5. Dark violet-colored flowers positioned on strong and erect peduncles.
6. Good garden performance.

Plants of the new *Lavandula* differ primarily from plants of the female parent, 'Felice', in flower color as plants of the new *Lavandula* have dark violet-colored flowers whereas plants of 'Felice' have light blue-colored flowers. In addition, plants of the new *Lavandula* are not as strongly upright as plants of 'Felice'.

Plants of the new *Lavandula* can be compared to plants of *Lavandula angustifolia* 'sako1644', disclosed in a U.S. Plant Patent application filed concurrently. Plants of the new *Lavandula* differ from plants of 'sako1644' primarily in flower color as plants of the new *Lavandula* have darker violet-colored flowers than plants of 'sako1644'. In addition, plants of the new *Lavandula* are more upright and narrower than plants of 'sako1644'.

Plants of the new *Lavandula* can be compared to plants of the *Lavandula angustifolia* 'Annet', disclosed in U.S. Plant Pat. No. 28,867. In side-by-side comparisons, plants of the new *Lavandula* differ primarily from plants of 'Annet' in the following characteristics:

1. Plants of the new *Lavandula* are not as compact as plants of 'Annet'.
2. Plants of the new *Lavandula* are not as strongly upright as plants of 'Annet'.

Plants of the new *Lavandula* can be compared to plants of the *Lavandula angustifolia* 'Blue Royalty', disclosed in U.S. Plant Pat. No. 20,657. In side-by-side comparisons, plants of the new *Lavandula* differ primarily from plants of 'Blue Royalty' in the following characteristics:

1. Plants of the new *Lavandula* are not as compact as plants of 'Blue Royalty'.
2. Plants of the new *Lavandula* are not as strongly upright as plants of 'Blue Royalty'.
3. Plants of the new *Lavandula* have dark violet-colored flowers whereas plants of 'Blue Royalty' have dark purple-colored flowers.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1 of 2) is a side perspective view of a typical flowering plant of 'sako1638' grown in a container.

Figure 2:
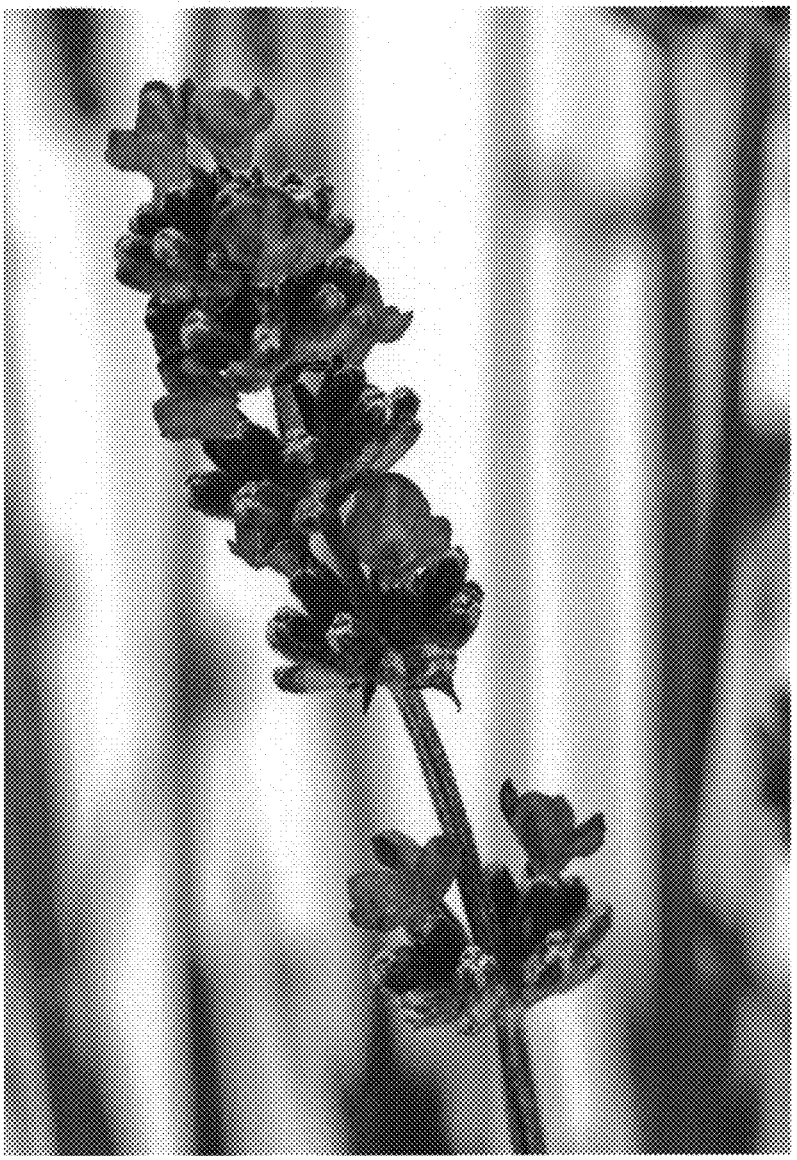

The photograph on the second sheet (FIG. 2 of 2) is a close-up view of a typical flowering plant of 'sako1638'.

DETAILED BOTANICAL DESCRIPTION

Plants used in the aforementioned photographs and following detailed description were grown in 17-cm containers during the spring and early summer in an outdoor nursery in Boskoop, The Netherlands after being grown in a glass-covered greenhouse during the winter and under cultural practices typical of commercial *Lavandula* production. Plants were pinched one time and were eight months old when the photographs and description were taken. During the production of the plants, day temperatures ranged from 10° C. to 30° C. and night temperatures ranged from 5° C. to 20° C. In the following description, color references are made to The Royal Horticultural Society Colour Chart, 2015 Edition, except where general terms of ordinary dictionary significance are used.

Botanical classification: *Lavandula angustifolia* 'sako1638'.

Parentage:

*Female, or seed, parent.*—*Lavandula angustifolia* 'Felice', not patented.

*Male, or pollen, parent.*—Unknown proprietary selection of *Lavandula angustifolia*, not patented.

Propagation:

*Type.*—Vegetative stem cuttings.

*Time to initiate roots, summer and winter.*—About ten days at temperatures about 18° C.

*Time to produce a rooted young plant, summer.*—About 60 days at temperatures about 20° C.

*Time to produce a rooted young plant, winter.*—About 70 days at temperatures about 20° C.

*Root description.*—Fine, fibrous; initially white in color and becoming more brown with development; actual color of the roots is dependent on substrate composition, water quality, fertilizer type and formulation.

*Rooting habit.*—Freely branching; dense.

Plant description:

*Plant and growth habit.*—Herbaceous perennial; compact and upright plant habit; broadly oblong to narrowly obovate in overall plant shape; strong and sturdy plants; freely branching habit; moderately vigorous to vigorous growth habit; moderate growth rate; flowers arranged in terminal spikes.

*Plant height, soil level to top of foliar plane.*—About 21.7 cm.

*Plant height, soil level to top of floral plane.*—About 38.5 cm.

*Plant width.*—About 34.2 cm.

*Lateral branch description.*—Quantity per plant: About ten primary lateral branches each with about ten secondary lateral branches developing per plant; pinching enhances lateral branch development. Length: About 11.7 cm. Diameter: About 2 mm. Internode length: About 1.9 cm. Strength: Moderately strong. Aspect: About 30° from vertical. Texture and luster: Dense glandular pubescence; matte. Color, when developing: Close to 145B. Color, developed: Close to between 137C and 147B; when woody, close to N199C.

*Leaf description.*—Arrangement: Opposite, simple; sessile. Quantity per lateral branch: About 14. Length: About 3.6 cm. Width: About 5 mm. Shape: Narrowly oblanceolate; moderately carinate. Apex: Bluntly acute to obtuse. Base: Broadly cuneate. Margin: Entire; slightly to moderately revolute; not lobed. Texture and luster, upper surface: Moderately pubescent, glandular; slightly glossy. Texture and luster, lower surface: Moderately to densely pubescent, glandular; matte. Fragrance: Strongly aromatic, pungent. Venation pattern: Pinnate. Color: Developing leaves, upper surface: Close to 138A. Developing leaves, lower surface: Close to 143C. Fully expanded leaves, upper surface: Close to NN137B; venation, close to 138B. Fully expanded leaves, lower surface: Close to 144B; venation, close to 143A.

Flower description:

*Flower type, arrangement and habit.*—Small single salverform flowers arranged on terminal spikes; freely flowering, about 70 flowers developing per inflorescence and more than 6,500 flowers developing per plant during the flowering season; flowers with two-lobed upper lip and three-lobed lower lip; flowers face mostly outwardly on the spike.

*Natural flowering season.*—Long flowering period; continuous from late spring into late summer in The Netherlands; plants begin flowering about 13 weeks after planting.

*Flower longevity on the plant.*—Individual flowers last about four weeks on the plant; flowers not persistent.

*Fragrance.*—None detected.

*Flower buds.*—Length: About 6 mm. Diameter: About 3 mm. Shape: Oblong. Texture and luster: Densely tomentose; matte. Color: Close to 86A; pubescence, close to 86A.

*Inflorescence size.*—Height: About 6.4 cm. Diameter: About 2 cm.

*Flower size.*—Diameter: About 7 mm by 7 mm. Depth (height): About 1.1 cm. Throat diameter: About 1.5 mm. Tube length: About 6.5 mm. Tube diameter: About 1.75 mm.

*Petals.*—Quantity and arrangement: Upper lip, two-lobed and lower lip, three-lobed. Length, upper lip: About 1.1 cm. Length, lower lip: About 1 cm. Width, upper lip: About 4 mm. Width, lower lip: About 3 mm. Shape: Roughly spatulate; upper lip is 60% fused into a tube and lower lip is 65% fused into a tube. Apex: Obtuse, rounded. Margin: Entire; moderately undulate. Texture and luster, upper and lower surfaces: Smooth, glabrous; moderately velvety; matte. Texture and luster, throat: Smooth, glabrous; matte. Texture and luster, tube: Moderately pubescent; matte. Color: When opening, upper surface: Close to 86A to 86B. When opening, lower surface: Close to N82B. Fully opened, upper surface: Close to 86B, fading towards the throat to close to N87B; venation, similar to lamina colors; color does not change with development. Fully opened, lower surface: Close to 86C; venation, similar to lamina colors; color does not change with development. Throat: Close to N87B; venation, close to N87B. Tube: Close to N87B, fading towards the base to close to NN155D; venation, similar to lamina colors.

*Sepals.*—Quantity and arrangement: Five, fused into a campanulate tube; lower 90% of sepals are fused. Length: About 5 mm. Width: About 1 mm. Shape: Lanceolate. Apex: Broadly acute. Margin: Entire. Texture and luster, upper and lower surfaces: Densely pubescent; matte. Color: When opening and fully opened, upper surface: Close to 147C; venation, close to NN137A. When opening and fully opened, lower surface: Close to 86A.

*Flower bracts.*—Quantity and arrangement: One bract positioned at the base of each group of about seven flowers. Length: About 4 mm. Width: About 4 mm. Shape: Broadly rhomboidal. Apex: Narrowly apiculate. Base: Cuneate. Margin: Finely dentate. Texture and luster, upper and lower surfaces: Slightly pubescent, glandular; slightly glossy. Color, upper and lower surfaces: Close to 199B; venation, close to 200A.

*Peduncles.*—Length: About 19.4 cm. Diameter: About 2 mm. Aspect: Mostly upright. Strength: Strong. Texture and luster: Moderately to densely pubescent, glandular; matte. Color: Close to between 137C and 138A.

*Pedicels.*—Length: About 1.75 mm. Diameter: About 1.75 mm. Aspect: About 30° to 45° from peduncle axis. Strength: Moderately strong. Texture and luster: Densely pubescent; matte. Color: Close to N77C.

*Reproductive organs.*—Stamens: Quantity per flower: Four. Filament length: About 2 mm. Filament color: Close to NN155C. Anther shape: Reniform. Anther size: About 0.5 mm by 0.5 mm. Anther color: Close to 203A. Pollen amount: Moderate. Pollen color: Close to 21B. Pistils: Quantity per flower: One. Pistil length: About 5 mm. Stigma shape: Club-shaped. Stigma size: About 0.4 mm by 0.1 mm. Stigma color: Close to 156D, distally, close to 15A. Style length: About 4 mm. Style color: Close to NN155D. Ovary color: Close to 146C.

*Seeds and fruits.*—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be suitable for USDA Hardiness Zones 6 to 10.

It is claimed:

1. A new and distinct *Lavandula* plant named 'sako1638' as illustrated and described.

* * * * *